US012629143B2

(12) United States Patent　　　(10) Patent No.:　US 12,629,143 B2
Chappuis　　　　　　　　　　　　　(45) Date of Patent:　May 19, 2026

(54) APPARATUS AND METHOD FOR REPAIR OF DURAL TEAR

(71) Applicant: CHAP-MED, INC., Destin, FL (US)

(72) Inventor: James L. Chappuis, Hollywood, FL (US)

(73) Assignee: CHAP-MED, INC., Destin, FL (US)

( * ) Notice: Subject to any disclaimer, the term of this patent is extended or adjusted under 35 U.S.C. 154(b) by 252 days.

(21) Appl. No.: 18/327,435

(22) Filed: Jun. 1, 2023

(65) Prior Publication Data

US 2024/0398398 A1　　Dec. 5, 2024

(51) Int. Cl.
A61B 17/02　　　(2006.01)
A61B 17/34　　　(2006.01)

(52) U.S. Cl.
CPC ........ A61B 17/025 (2013.01); A61B 17/3423 (2013.01); *A61B 2017/0262* (2013.01); *A61B 2017/3429* (2013.01)

(58) Field of Classification Search
CPC ....... A61B 17/02; A61B 17/025; A61B 17/34; A61B 17/3423; A61B 17/04; A61B 17/0493; A61B 90/08
See application file for complete search history.

(56) References Cited

U.S. PATENT DOCUMENTS

| | | |
|---|---|---|
| 5,026,373 A | 6/1991 | Ray et al. |
| 5,047,030 A | 9/1991 | Draenert |
| 5,209,450 A | 5/1993 | Grapes |

| | | |
|---|---|---|
| 5,513,838 A | 5/1996 | Van Rossum |
| 5,649,945 A | 7/1997 | Ray et al. |
| 5,728,159 A | 3/1998 | Stroever et al. |
| 5,741,261 A | 4/1998 | Moskovitz et al. |
| 5,753,456 A | 5/1998 | Naqui et al. |
| 5,797,909 A | 8/1998 | Michelson |
| 5,803,904 A | 9/1998 | Mehdizadeh |
| 5,871,484 A | 2/1999 | Spievack et al. |
| 5,971,987 A | 10/1999 | Huxel et al. |
| 6,007,487 A | 12/1999 | Foley et al. |
| 6,045,579 A | 4/2000 | Hochshuler et al. |
| 6,080,193 A | 6/2000 | Hochshuler et al. |

(Continued)

FOREIGN PATENT DOCUMENTS

| | | |
|---|---|---|
| JP | 751292 | 2/1995 |
| JP | 07222752 | 8/1995 |

(Continued)

OTHER PUBLICATIONS

Extended European Search Report dated Sep. 19, 2024 in co-pending EP Application No. 24179425.4.

*Primary Examiner* — Christopher J Beccia
(74) *Attorney, Agent, or Firm* — Perilla Knox Hildebrandt Staley & Amy LLP; Stephanie L. Davy-Jow; Bradley K. Groff

(57) ABSTRACT

The present disclosure relates generally to a device and method for aiding in the repair of a dural tear. According to example embodiments, the device is placed substantially within a dural sac interior to a dural tear. The device provides a shield that prevents the underlying nerve roots (including rootlets) of the spinal cord from intruding into the torn area and prevents them from being injured during the repair procedure. The device also redirects cerebrospinal fluid from the area, which aids the surgeon in viewing the procedure site during suturing and/or repair.

19 Claims, 5 Drawing Sheets

(56) References Cited

U.S. PATENT DOCUMENTS

| | | | |
|---|---|---|---|
| 6,149,033 A | 11/2000 | Poleshuk |
| 6,231,577 B1 | 5/2001 | Canedy |
| 6,261,295 B1 | 7/2001 | Nicholson et al. |
| 6,356,325 B1 | 3/2002 | Shimoshikiryo |
| 6,379,385 B1 | 4/2002 | Kalas et al. |
| 6,383,221 B1 | 5/2002 | Scarborough et al. |
| 6,425,920 B1 | 7/2002 | Hamada |
| 6,500,180 B1 | 12/2002 | Foley et al. |
| 6,517,544 B1 | 2/2003 | Michelson |
| 6,524,320 B2 * | 2/2003 | DiPoto ............... A61B 17/3439 |
| | | 606/108 |
| 7,198,598 B2 | 4/2007 | Smith et al. |
| 7,214,186 B2 | 5/2007 | Ritland |
| 7,226,413 B2 | 6/2007 | McKinley |
| 7,625,374 B2 | 12/2009 | Branch et al. |
| 7,648,512 B2 | 1/2010 | Foley et al. |
| 7,815,649 B2 | 10/2010 | Layne et al. |
| 7,887,565 B2 | 2/2011 | Michelson |
| 8,100,917 B2 | 1/2012 | Foley et al. |
| 8,388,525 B2 | 3/2013 | Poo et al. |
| 2001/0010021 A1 | 7/2001 | Boyd et al. |
| 2002/0049368 A1 | 4/2002 | Ritland |
| 2002/0082604 A1 | 6/2002 | Abdelgany et al. |
| 2002/0120346 A1 | 8/2002 | Boyer et al. |
| 2002/0161449 A1 | 10/2002 | Muschler |
| 2003/0032966 A1 | 2/2003 | Foley et al. |
| 2003/0039676 A1 | 2/2003 | Boyce et al. |
| 2003/0195520 A1 | 10/2003 | Boyd et al. |
| 2003/0199874 A1 | 10/2003 | Michelson |
| 2003/0236447 A1 | 12/2003 | Ritland |
| 2004/0002711 A1 | 1/2004 | Berry |
| 2004/0002712 A1 | 1/2004 | Grinberg et al. |
| 2004/0138534 A1 | 7/2004 | Ritland |
| 2004/0225228 A1 | 11/2004 | Ferree |
| 2005/0107671 A1 | 5/2005 | McKinley |
| 2005/0154396 A1 | 7/2005 | Foley et al. |
| 2005/0154460 A1 | 7/2005 | Yundt |
| 2005/0165408 A1 | 7/2005 | Puno et al. |
| 2005/0228233 A1 | 10/2005 | Ritland |
| 2005/0261681 A9 | 11/2005 | Branch |
| 2006/0004261 A1 | 1/2006 | Douglas |
| 2006/0052670 A1 | 3/2006 | Stearns et al. |
| 2006/0084992 A1 | 4/2006 | Michelson |
| 2006/0106462 A1 | 5/2006 | Tsou |
| 2006/0142762 A1 | 6/2006 | Michelson |
| 2006/0200138 A1 | 9/2006 | Michelson |
| 2006/0200139 A1 | 9/2006 | Michelson |
| 2006/0200164 A1 | 9/2006 | Michelson |
| 2007/0038032 A1 | 2/2007 | De Canniere et al. |
| 2007/0123890 A1 | 5/2007 | Way et al. |
| 2007/0156020 A1 | 7/2007 | Foley et al. |
| 2008/0108876 A1 | 5/2008 | Houser |
| 2008/0132764 A1 | 6/2008 | Hamada |
| 2008/0221628 A1 | 9/2008 | Milbocker et al. |
| 2008/0255564 A1 | 10/2008 | Michelson |
| 2008/0287955 A1 | 11/2008 | Michelson |
| 2008/0300601 A1 | 12/2008 | Fabian |
| 2010/0241127 A1 | 9/2010 | Foley et al. |
| 2011/0087231 A1 | 4/2011 | Perri |
| 2011/0098705 A1 * | 4/2011 | Chappuis ............. A61B 17/025 |
| | | 606/53 |
| 2011/0245620 A1 | 10/2011 | Hamada |
| 2012/0010471 A1 | 1/2012 | Mire et al. |
| 2012/0197279 A1 | 8/2012 | Perez-Cruet et al. |
| 2013/0053851 A1 | 2/2013 | Schmitz et al. |
| 2015/0005614 A1 | 1/2015 | Heggeness et al. |
| 2015/0343205 A1 | 12/2015 | Howard et al. |

FOREIGN PATENT DOCUMENTS

| | | |
|---|---|---|
| JP | 09149906 | 6/1997 |
| JP | 10211213 | 8/1998 |

* cited by examiner

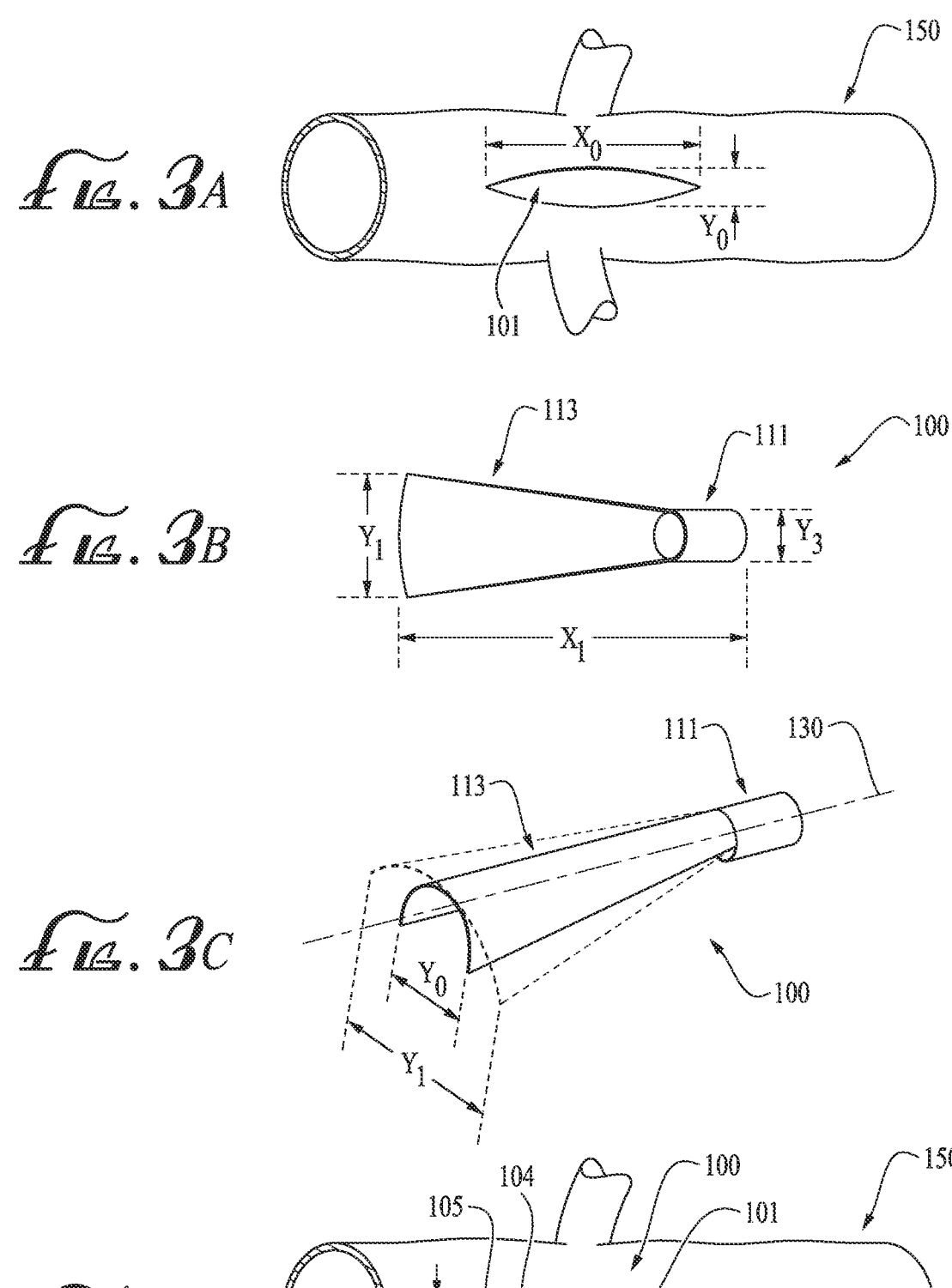
$fig. 3A$
$fig. 3B$
$fig. 3C$
$fig. 3D$

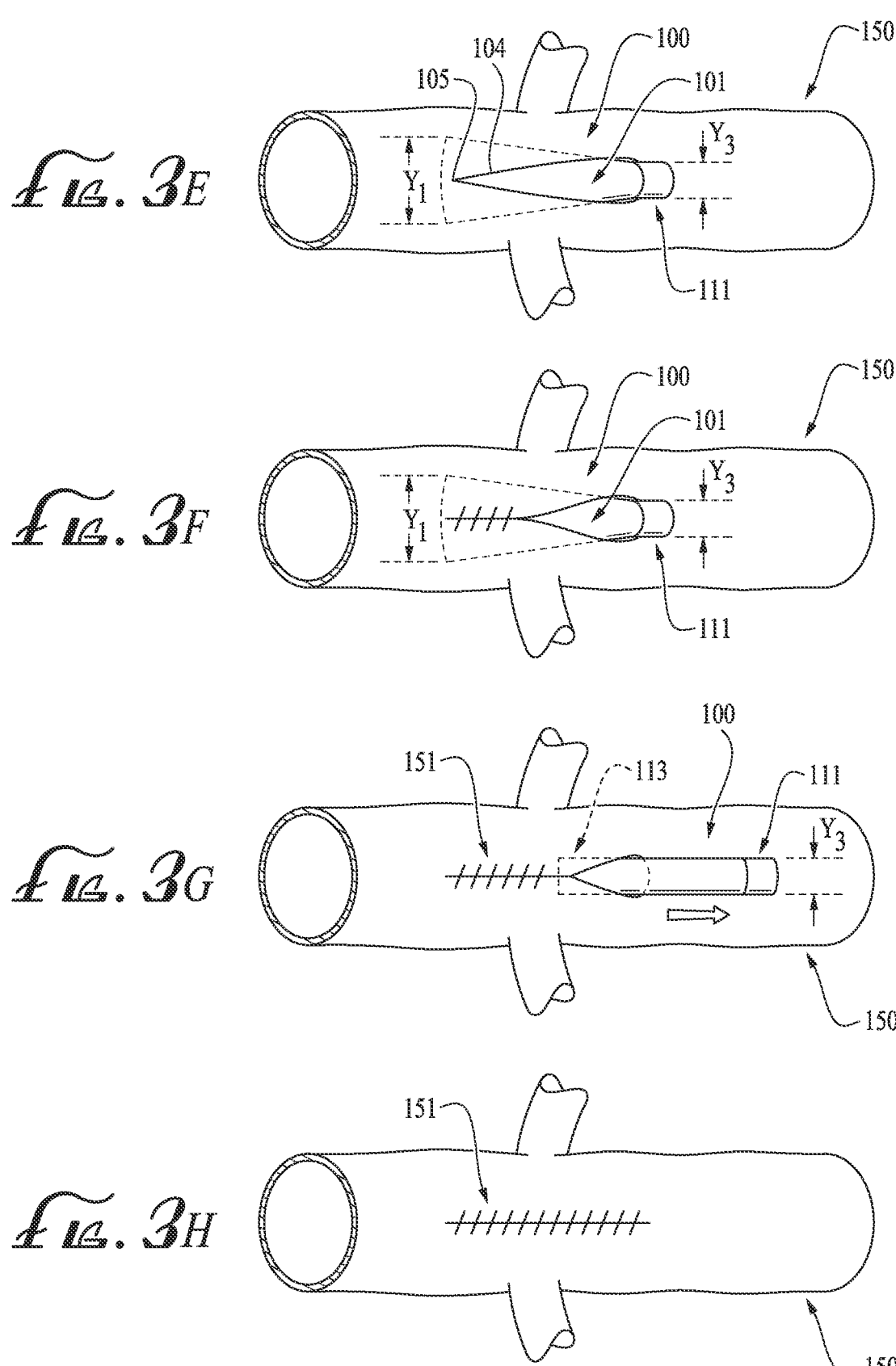

APPARATUS AND METHOD FOR REPAIR OF DURAL TEAR

TECHNICAL FIELD

The present invention relates generally to the field of spinal surgery, and more particularly to an apparatus and method for repair of a dural tear.

CROSS-REFERENCE AND INCORPORATION BY REFERENCE

U.S. Pat. Nos. 8,979,748 and 9,439,640 are hereby incorporated by reference herein.

BACKGROUND

The spinal cord is encompassed by the protective thecal sac, or dural sac, which is comprised of many layers. The outermost layer is known as the dura mater, and is often referred to as the dura. The innermost layer is the pia mater, which closely follows and envelops the spinal cord. Between the dura and the pia mater lies the arachnoid mater. Throughout the dural sac are several sets of nerve roots and rootlets that traverse the various layers. The dural sac also contains cerebrospinal fluid, or CSF, which acts as a shock absorber for the spinal cord.

During spinal procedures, the dural sac may be cut, torn, or otherwise perforated, which may lead to a leak of CSF fluid from the dural sac as well as other complications. In some cases, the perforations may heal on their own, but in other cases, surgical intervention is required. Surgical repair can be complicated by the presence of nerve roots within the area of the tear, which obstructs the torn area making suturing difficult and puts the roots and rootlets at risk of damage by surgical instrument. Additionally, the presence of CSF within the torn area can make suturing or stitching difficult.

Accordingly, it can be seen that needs exist for a protective apparatus and method for repair of dural tears. It is to the provision of a protective apparatus and method for repair of dural tears meeting these and other needs that the present invention is primarily directed.

SUMMARY

The present disclosure relates generally to a device and method for aiding in the repair of a dural tear. According to example embodiments, the device is placed substantially within a dural sac interior to a dural tear. The device provides a shield that prevents the underlying nerve roots (including rootlets) of the spinal cord from intruding into the torn area and prevents them from being injured during the repair procedure. The device also redirects cerebrospinal fluid from the area, which aids the surgeon in viewing the procedure site during suturing and/or repair.

In one aspect, the present invention relates to a device for use during repair of a dural tear, the device comprising a substantially tubular section having a first end and a second end, and a flexible shield section having a first end and a second end, the second end connecting to the tubular section first end, wherein the shield section first end is wider than the second end of the shield section when no external loads are applied to the first end, and the second end of the shield section is curved so as to form a circular or semi-circular shape with substantially the same radius as the tubular section.

In some embodiments, the device is configured to be placed substantially within the dural sac. In example embodiments, the device may be made from silicone. In specific embodiments, the device may be made from Silastic material. In certain embodiments, the device prevents the nerve roots and rootlets within the dural sac from coming within the vicinity of a dural tear. In yet further embodiments, the placement of the device allows the passage of cerebrospinal fluid from the dural sac through the substantially tubular section. In some embodiments, the first end of the shield section has a radius of curvature that is larger than the radius of curvature of the second end of the shield section. In other embodiments, the first end of the flexible shield section is substantially flat when no external loads are applied to the flexible shield section.

In another aspect, the invention relates to a method of repairing a dural tear, the method comprising placing a device within a perforated section of a dural sac, placing sutures along the dural sac, and removing the device from the dural sac. The device within the method comprises a substantially tubular section having a first end and a second end, and a flexible shield section having a first end and a second end. The shield section second end connects to the tubular section first end. The shield section first end is wider than the shield section second end when no external loads are applied to shield section, and the second end of the shield section is curved so as to form a circular or semi-circular shape with substantially the same radius as the tubular section.

In example embodiments of the method, the device is made from silicone. In other embodiments of the method, the device is made from Silastic material. In particular embodiments of the method, the placement of the device prevents nerve roots and rootlets within the dural sac from coming within the vicinity of a dural tear. In specific embodiments of the method, the placement of the device allows the passage of cerebrospinal fluid from the dural sac through the substantially tubular section. In yet further embodiments, the first end of the shield section has a radius of curvature that is larger than the radius of curvature of the second end of the shield section. In other embodiments, the first end of the flexible shield section is substantially flat when no external loads are applied to the flexible shield section. In certain embodiments, the method further comprises the step of folding the flexible shield section so as to reduce the maximum width of the device. In further embodiments, the method further comprises the step of allowing the shield section to expand once it is within the dural sac. In yet further embodiments, the method comprises the step of allowing the shield section to decrease in width as it is removed from the dural tear.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of example embodiments are explanatory of example embodiments of the invention, and are not restrictive of the invention, as claimed.

BRIEF DESCRIPTION OF THE DRAWINGS

FIGS. 3A-E (collectively FIG. 3) show an example method of use of the device according to an example embodiment of the present invention, with FIG. 3A showing an example dural sac having a dural tear needing repair.

FIG. 3B shows the step of selecting an appropriately sized device according to an example embodiment of the method.

FIG. 3C shows the step of folding the device according to an example embodiment of the method.

FIG. 3D shows the step of inserting the device into the dural sac according to an example embodiment of the method.

FIG. 3E shows the step of allowing the device to expand within the dural sac according to an example embodiment of the method.

FIG. 3F shows the step of suturing the dural sac once the device has been placed within the dural sac according to an example embodiment of the method.

FIG. 3G shows the step of removing the device from the dural sac once sutures have been placed according to an example embodiment of the method.

FIG. 3H shows the step of placing the final sutures once the device has been removed from the dural tear according to an example embodiment of the method.

DETAILED DESCRIPTION OF EXAMPLE EMBODIMENTS

The present invention may be understood more readily by reference to the following detailed description of example embodiments taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1A:
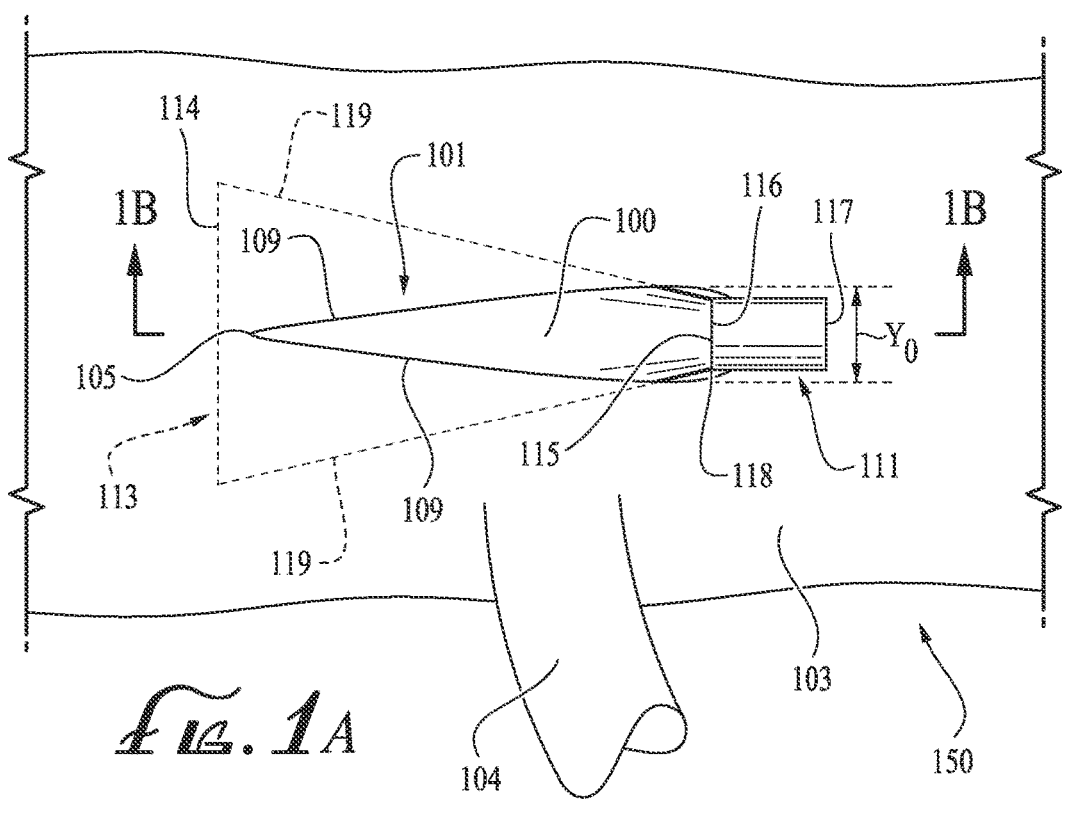
FIG. 1A is a top view of a device according to an example embodiment of the present invention shown within a dural sac.
Figure 1B:
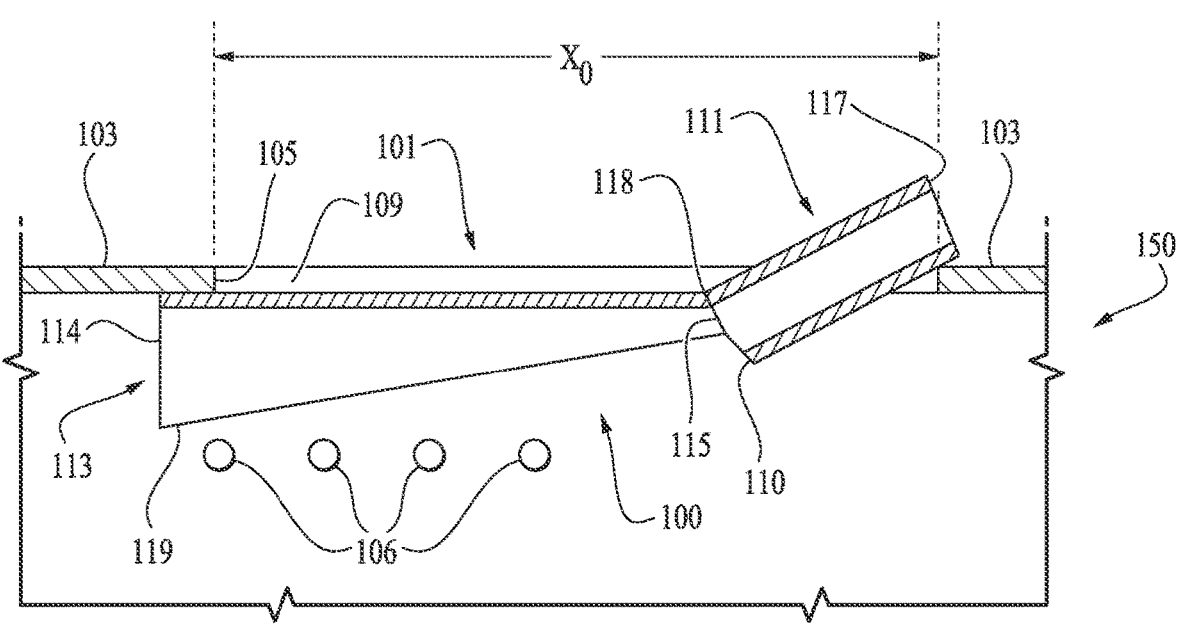
FIG. 1B is a cross-sectional view of the device within the dural sac taken at line 1B-1B of FIG. 1A.

With reference now to the drawing figures, wherein like reference numbers represent corresponding parts throughout the several views, FIGS. 1A-B show a dural sac 150 with an example protective shield device 100 placed within a dural tear 101 of dura mater 103. The device 100 includes a tube section 111 connected to a shield section 113. The shield section 113 has a distal shield section first end 114 and a proximal shield section second end 115, with shield section edges 119 extending between the two ends. The tube section 111 has a distal tube section first end 116 and a proximal tube section second end 117. The shield section second end 115 joins with the tube section first end 116 at intersection 118.

FIGS. 2A-D also show the device of FIG. 1, inverted about its longitudinal axis to better illustrate and describe the device. In the embodiment shown in FIGS. 1 and 2, the shield section 113 is comprised of a sheet of flexible silicon material, such as Silastic sheeting, suitable for insertion into the dural sac 150. The material properties of the flexible silicone material are such that the shield section 113 is flexible enough to be deformed (e.g., rolled and/or folded) while being rigid enough to deflect and or resist penetration by surgical instruments. The flexibility of the silicone material also allows the shape of the shield section 113 to be manipulated by a surgeon, either manually or with surgical instruments, and to conform to the non-uniform shape of the dural sac 150 and/or the dural tear 101. In other embodiments, the shield section may be formed from another type of material.

In particular embodiments, shield section 113 of the device 100 may be formed from a section of material and optionally trimmed (e.g., cut) to the necessary size needed for surgery before it is mated with the tubular section 111. The material may be selected from various materials, including silicone materials, with different thicknesses, stiffnesses, and other material properties. In the embodiment shown in FIGS. 1 and 2, the material forming shield section 113 has a trapezoidal shape, resulting in the shield section 113 having a wider shield section first end than the shield section second end. In other embodiments, the material forming shield section 113 may be cut into square shapes, or another regular or irregular shape.

Figure 2A:
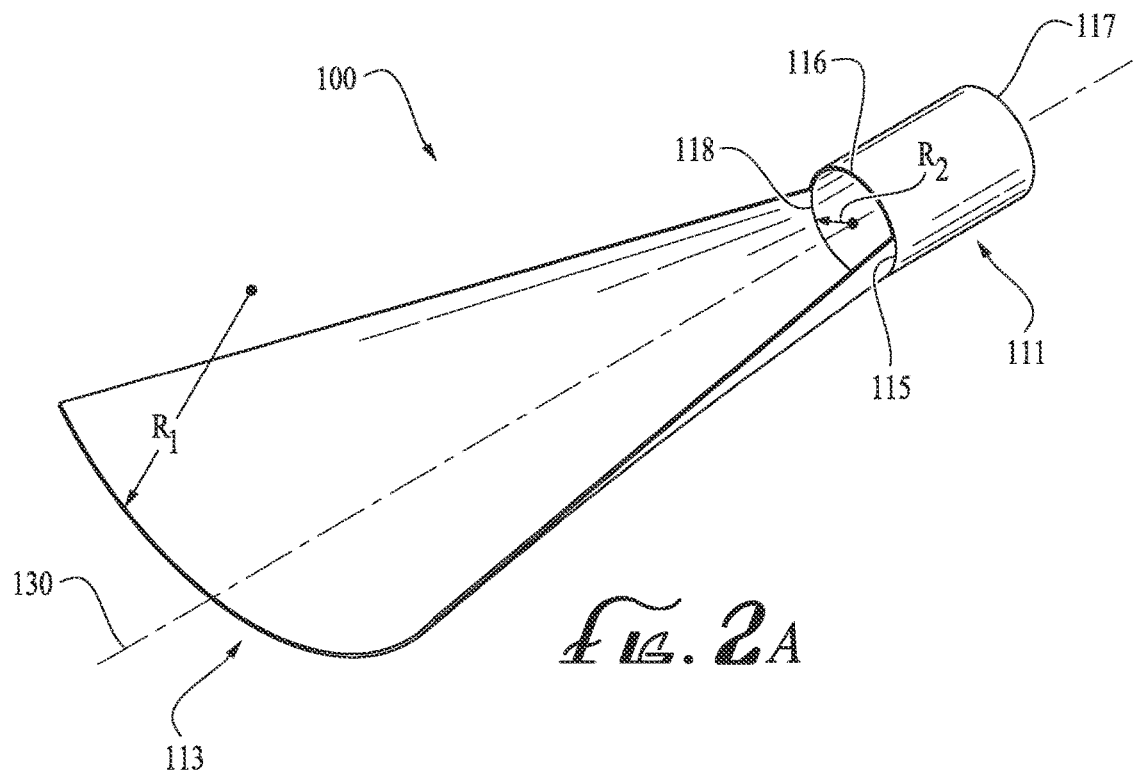
FIG. 2A is a perspective view of the bottom side of the device of FIG. 1A.
Figure 2B:
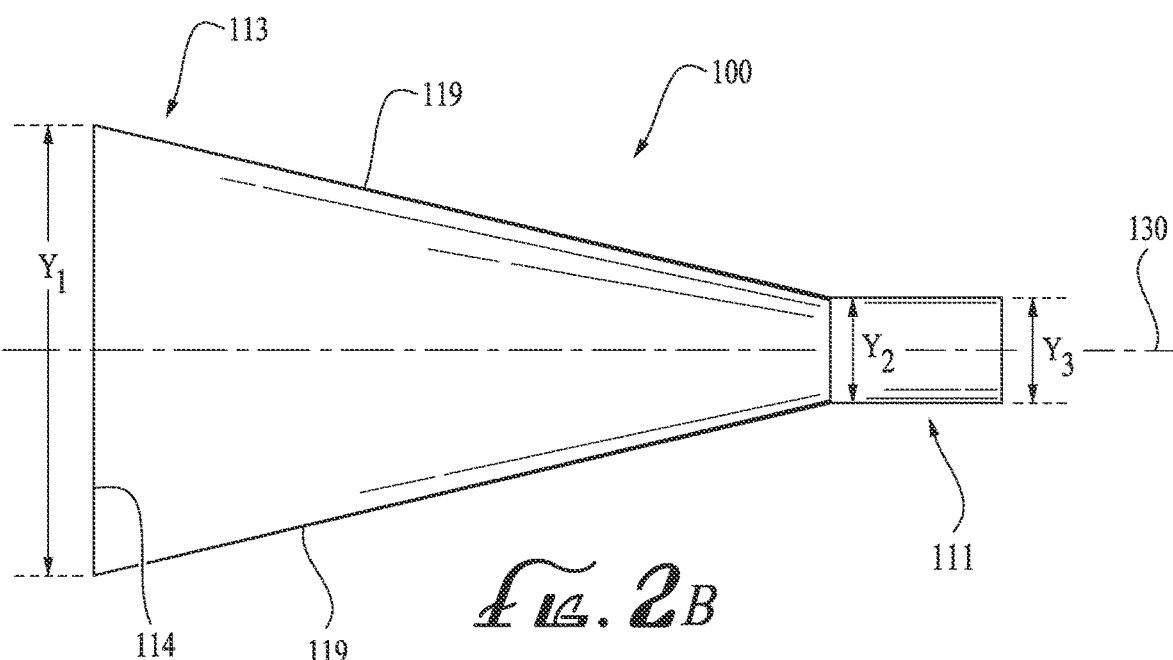
FIG. 2B is a bottom view of the device of FIG. 1A.
Figure 2C:
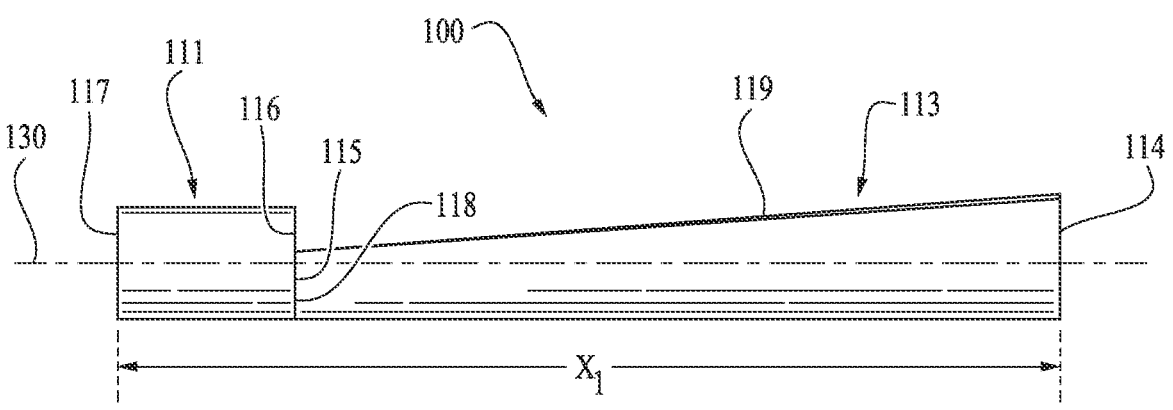
FIG. 2C is a side view of the device of FIG. 1A.
Figure 2D:
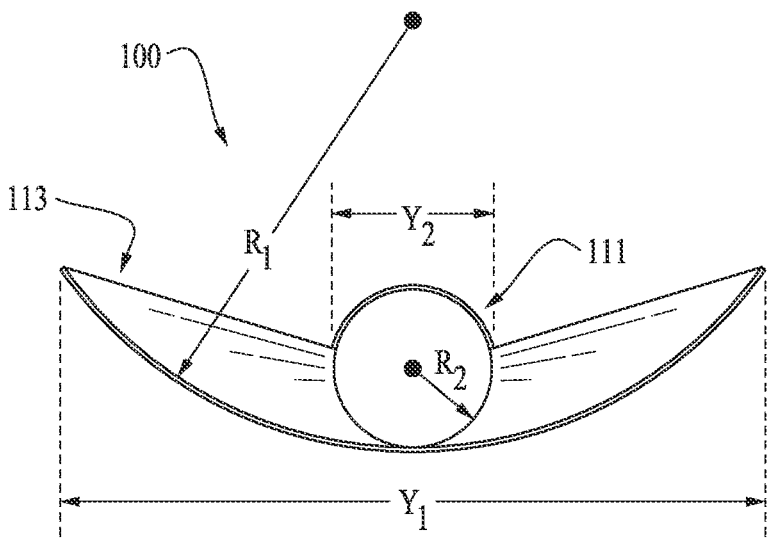
FIG. 2D is a front view of the device of FIG. 1A.

As better shown in FIGS. 2A and 2D, in particular embodiments, the flexible material forming shield section 113 is biased towards a flat shape such that unconstrained shield section first end 114 tends towards the flat shape while the shield section second end 115 is forced into a circular shape (and held there) due to the connection with the tube section 111. This results in the shield section first end 114 having a larger radius of curvature R1 than the shield section second end 115 radius of curvature R2. In other embodiments, however, the shield section 113 may be biased to a curved shape, which may or may not change the relative size of the shield section first end 114 radius of curvature R1 and the shield section second end 115 radius of curvature R2.

As best shown in FIGS. 2A-D, the device 100 has a length X1 measured from the shield section first end 114 to the tube section second end 117 about a reference longitudinal axis 130. The length X1 of the device may be determined based on the length X0 of the dural tear 101, but in example embodiments, X1 is about 3 cm to about 8 cm (e.g., about 5 cm). The shield section 113 has a variable width measured from the reference axis 130 to the shield section edges 119 on a plane perpendicular to the reference axis 130. The width of the shield section 113 tapers such that the shield section first end 114 has a first width Y1 that is greater than width Y2 at the shield section second end 115. In other embodiments, the shield section 113 the shield section need not taper, or may be wider at the wider at shield section second end 115 than the shield section first end 114. The width of the device may be determined based on the width of the dural 101, but in example embodiments, Y1 is about 1 cm to about 2 cm (e.g., about 1.5 cm).

As shown in the embodiment of FIG. 1 and FIG. 2, the tube section 111 forms a passageway between the tube section first end 116 and the tube section 117. The tube section 111 of the embodiment of the device 100 shown in this embodiment comprises a piece of silicone material, such as Silastic material, shaped into a tube. In some embodiments, the tube section is formed from a sheet of silicone material that has been glued, welded, taped, bolted, or otherwise joined to itself to form a tube shape. In other embodiments, the tube section 111 is preformed (e.g., extruded) into a tube shape. In the embodiment shown in FIGS. 1 and 2, the tube section 111 has a diameter Y3 that is substantially the same as or slightly larger than the width Y0 of the dural tear 101, but in example embodiments, the diameter Y3 of the tube section may be about 0.5 cm. In some embodiments, the tube section 111 may have a variable diameter between the tube section first end 116 and the tube section second end 117.

In some embodiments, the shield section 113 and the tube section 111 are formed separately and joined together at interface 118 by gluing, welding, taping, or otherwise fixing the two sections together. In other embodiments, the shield section second end 113, may be glued welded, or taped so as to form the tubular section 111. In some embodiments, the tube section 111 is formed so that it envelops the shield section second end 115 within the tube section 111. In yet further embodiments, the shield section 113 envelops the tube section 111. In certain embodiments, the device 100 may be prefabricated in a selection of shapes, sizes, and material properties. In particular embodiments, the device 100 may be integrally formed by molding, additive manufacturing, or other appropriate process.

In example embodiment shown in FIG. 1, the length X1 of the device 100 is greater than the length X0 of the dural tear 101, and the width Y1 at the shield section first end 114 is greater than the maximum width Y0 of the dural tear 101. The larger length X1 and width Y1 of the device 100 allows it to span all or substantially all of the open area created by the dural tear 101 within the dural sac 150. In other embodiments, the length X1 may be the same or shorter than the length X0 of the dural tear 101. In some embodiments, the width Y1 at the shield section first end 114 may be less than the maximum width Y0 of the dural tear 101.

In the embodiment shown in FIG. 1, the device 100 is placed within the dural sac 150 such that the shield section first end 114 and substantially all of the shied section edges 119 are positioned interior to the dura 103 and extend laterally beyond the dural tear edge 109. In other embodiments the shield section first end 114 and/or the shield section edges may not extend beyond the dural tear edge 109. In the embodiment shown in FIG. 1, the tubular section 111 is positioned such that the tubular section first end 116 extends interior to or beneath the surface of the dura 103, while the tubular section second end 117 remains at or exterior to the surface of the dura 103. The flexibility of the shield section allows 113 allows the tube section 111 to be placed at an angle relative to the shield section 113. In other embodiments, the tube section 111 need not be placed at an angle relative to the shield section 113. In particular embodiments, the tube section 111 may be completely interior to, or exterior to the dura 103.

The placement of the protective shield section 113 of the device 100 beneath the dura 103 prevent the roots 104 and rootlets 106 from intruding into the area of the dural tear 101 and shields the nerve roots 104 and rootlets 106 from contact with the surgical instruments. This helps to prevent any accidental injury during repair of the dural tear 101. The shield section 113 also provides a barrier between CSF fluid within the dural sac 150 and the dural tear 101. In particular embodiments, such as the one shown in FIG. 1, the shield section 113 redirects the CSF fluid away from the dural tear 101 and through the tubular section 111. The absence of CSF fluid within the area of the tear 101 improves the surgeon's view of the tear 101 during surgery and facilitates suturing.

FIGS. 3A-H show an example procedure and method of use of the device 100. As shown in FIG. 3A, a dural sac 150 has a dural tear 101 in need of repair. During repair surgery, a surgeon or an assistant makes a determination as to the size and shape of device needed based on the size and shape of the dural tear 101, as well as other factors. In the example embodiment shown in FIG. 3A, the dural tear 101 has a length X0 and a maximum width Y0.

Once the size and shape of the dural tear are determined, an appropriately sized device 100, as shown in FIG. 3B, is formed from a silicone material or chosen from a selection of premanufactured devices as previously described. In the example embodiment shown in FIG. 3B, the device 100 is formed or chosen to have a length X1, a maximum width Y1 at the shield section first end 114, and a tube section 111 with a diameter Y3. The diameter Y3 of the tube section 111 is the minimum width of the device and is substantially the same as the maximum width of the dural tear 101. In this example, X1, Y1 are larger than the corresponding dural tear 101 dimensions, but in other examples, one or more of the device dimensions may be the same as or smaller than the tear dimensions.

As shown in FIG. 3C, once an appropriately sized device is acquired, the shield section 114 is deformed (e.g., rolled and/or folded) along a reference longitudinal axis 330 to reduce the maximum width Y1 of the shield section first end 114 to be the same as, or smaller than, that of the maximum width Y0 of the dural tear 101. The device is held in the rolled and/or folded configuration using forceps or other surgical instruments.

The device 100 is then placed into the dural tear 101 using forceps to first insert the rolled and/or folded shield section 113 through the edges of the dural tear with the shield section edges 119 pointing towards the interior of the dural sac 150. The device 100 is positioned such that all, or substantially all, of the shield section 101 is within the dural sac 150. As shown in FIG. 3D the device 100 is initially positioned such the shield section first end 314 extends slightly beyond the edge 105 of the dural tear 101, the tube section first end is interior to the dura 103, and the section 111 is at or above the surface of the dura 103.

As shown in FIG. 3E, once the device 100 is in position, the shield section 113 is allowed to expand. In this expanded position, the shield section 113 protects the roots and rootles within the dural sac 150 from injury from the operating instruments, and redirects CSF fluid away from the dural tear 101 and through the tube section 111.

As shown in FIG. 3F, with the device in position, sutures 151 are used to close the dural tear 301. The initial suture 151 is placed on the end of the dural tear 101 closes to the shield section first end 114, and the following sutures are placed increasingly closer to the tube section 111.

As shown in FIG. 3G, as the sutures are placed the device may be removed from the dural tear 301 by using forceps to pull the device 100 through the remaining opening in the dural tear 101. As the device 100 is removed, the unclosed edges of the dural tear 101 will cause the shield section 113 to fold again, reducing the maximum width Y1 of the shield section 113 such that it will fit through the remaining opening in the dural tear 101. In other embodiments, the surgeon may remove the device after all or nearly all the sutures have been placed. In particular embodiments, the surgeon may manually configure the device for removal, or the device may be formed such that it may be removed without further manipulation. As shown in FIG. 3H, once the device 100 is removed, additional sutures are placed to close the dural sac 150.

While the invention has been described with reference to example embodiments, it will be understood by those skilled in the art that a variety of modifications additions, and deletions are within the scope of the invention, as defined by the following claims.

What is claimed is:

1. A device for use during repair of a dural tear, the device comprising:

a substantially tubular section having a first end and a second end, and a spatulate flexible shield section having a first end and a second end, the second end of the shield section connecting to the tubular section first end, wherein the first end of the shield section is wider than the second end of the shield section when no external loads are applied to the shield section, and the second end of the shield section is curved so as to form a circular or semi-circular shape with substantially the same radius as the tubular section, and wherein the shield section is configured to bend along a longitudinal axis.

2. The device of claim 1, wherein the device is configured to be placed substantially within the dural sac.

3. The device of claim 1, wherein the device is made from silicone.

4. The device of claim 3, wherein the device is made from Silastic material.

5. The device of claim 1, wherein the placement of the device prevents nerve roots and rootlets within the dural sac from coming within the vicinity of a dural tear.

6. The device of claim 1, wherein the placement of the device allows the passage of cerebrospinal fluid from the dural sac through the substantially tubular section.

7. The device of claim 1, wherein the first end of the shield section has a radius of curvature that is larger than the radius of curvature of the second end of the shield section.

8. The device of claim 1, wherein the first end of the flexible shield section is substantially flat when no external loads are applied to the flexible shield section.

9. A method of repairing a dural tear, the method comprising:

placing a device within a perforated section of a dural sac; removing the device from the dural sac, wherein the device comprises, a substantially tubular section having a first end and a second end, and a spatulate flexible shield section having a first end and a second end, the shield section second end connecting to the tubular section first end, wherein the shield section first end is wider than the shield section second end when no external loads are applied to the shield section, and the second end of the shield section is curved so as to form a circular or semi-circular shape with substantially the same radius as the tubular section, and wherein the shield section is configured to bend along a longitudinal axis.

10. The method of claim 9, wherein the device is made from silicone.

11. The method of claim 10, wherein the device is made from Silastic material.

12. The method of claim 9, wherein the placement of the device prevents nerve roots and rootlets within the dural sac from coming within the vicinity of a dural tear.

13. The method of claim 9, wherein the placement of the device allows the passage of cerebrospinal fluid from the dural sac through the substantially tubular section.

14. The method of claim 9, wherein the first end of the shield section has a radius of curvature that is larger than the radius of curvature of the second end of the shield section.

15. The method of claim 9, wherein the first end of the flexible shield section is substantially flat when no external loads are applied to the flexible shield section.

16. The method of claim 9, the method further comprising the step of folding the flexible shield section so as to reduce the maximum width of the device.

17. The method of claim 16, the method further comprising the step of allowing the shield section to expand once it is within the dural sac.

18. The method of claim 17, the method further comprising the step of allowing the shield section to decrease in width as it is removed from the dural tear.

19. The method of claim 9, the method further comprising placing sutures along the dural sac prior to removing the device from the dural sac.

* * * * *